United States Patent
Abd-Elkader et al.

(10) Patent No.: US 12,011,473 B1
(45) Date of Patent: Jun. 18, 2024

(54) GREEN NANOPARTICLE COMPOSITION FOR TREATMENT OF HISTOPLASMOSIS

(71) Applicant: KING FAISAL UNIVERSITY, Al-Ahsa (SA)

(72) Inventors: Enas Mohamed Ali Abd-Elkader, Omaireyah-Hofouf (SA); Basem Mohamed Abdallah, Omaireyah-Hofouf (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/511,109

(22) Filed: Nov. 16, 2023

(51) Int. Cl.
*A61K 36/24* (2006.01)
*A61K 9/51* (2006.01)
*A61K 33/38* (2006.01)
*A61P 31/10* (2006.01)

(52) U.S. Cl.
CPC ............ *A61K 36/24* (2013.01); *A61K 9/51* (2013.01); *A61K 9/5192* (2013.01); *A61K 33/38* (2013.01); *A61P 31/10* (2018.01)

(58) Field of Classification Search
CPC ........ A61K 36/24; A61K 9/51; A61K 9/5192; A61K 33/38; A61P 31/10
See application file for complete search history.

(56) References Cited

U.S. PATENT DOCUMENTS

2014/0234454 A1  8/2014  Asiedu et al.

OTHER PUBLICATIONS

Alamier et al.; "Biosynthesis of Ag Nanoparticles Using Caralluma acutangula Extract and Its Catalytic Functionality towards Degradation of Hazardous Dye Pollutants" Crystals (2022); 12, 1069; published Jul. 30, 2022.*

Abdallah et al.; "Green Synthesis of Silver Nanoparticles Using the Lotus lalambensis Aqueous Leaf Extract and Their Anti-Candidal Activity against Oral Candidiasis"; ACS Omega; 6, pp. 8151-8162. Published Mar. 15, 2021.*

Llifle, The Encyclopedia of Succulents: *Caralluma retrospeciens* var. *acutangula* (Decne.) (Nov. 14, 2005). Most recent publication as of Sep. 16, 2019.*

Alyssa Ochs, "What Is Histoplasmosis and Natural Remedies for This Lung Infection", Seagateworld Website, First available online on Jan. 11, 2019.

Sivakumar S. Moni et al., "Assessment of Antifungal Properties of the Exudate Gel from the Stem of Caralluma retrospiciens Against Clinical Isolate of Candida albicans", Saudi Journal of Medical Pharmaceutical Sciences, pp. 562-565, First available online on Aug. 19, 2023.

WFO Plant List, "Snapshots of the taxonomy", Website, First available online on Dec. 2022.

Hortipedia, "Caralluma retrospiciens", Website; 2023.

* cited by examiner

Primary Examiner — Jeffrey T. Palenik

(74) Attorney, Agent, or Firm — Nath, Goldberg & Meyer; Richard C. Litman

(57) ABSTRACT

A composition of green biosynthesized silver nanoparticles made using leaf extract of *Desmidorchis retrospiciens*, as a novel antifungal therapy. These biosynthesized silver nanoparticles can be combined with leaf extract of *Desmidorchis retrospiciens* to provide a synergistic treatment for histoplasmosis.

GREEN NANOPARTICLE COMPOSITION FOR TREATMENT OF HISTOPLASMOSIS

BACKGROUND

1. Field

The disclosure of the present patent application relates to a composition of green biosynthesized silver nanoparticles made using leaf extract of *Desmidorchis retrospiciens*, as a novel antifungal therapy.

2. Description of the Related Art

Histoplasmosis, the most common endemic fungal infection disease, is caused by the fungus *Histoplasma capsulatum*. Exposure to a huge inoculum of conidia of *H. capsulatum* can lead to severe pulmonary infection. This scenario is also noted with patients taking corticosteroids, those having received a solid organ or hematopoietic cell transplant, and persons with HIV infection. The existing therapies typically use triazoles and the polyenes. However, there are often several severe side effects associated with use of these drugs and the cure rates are very low.

Thus, new treatments for histoplasmosis solving the aforementioned problems are desired.

SUMMARY

The present subject matter relates to a novel composition for the treatment of histoplasmosis. Specifically, the present subject matter relates to the inhibition of fungal growth by using a composition of green biosynthesized silver nanoparticles using leaf extract of *Desmidorchis retrospiciens* as a novel antifungal therapy, thus reducing side effects and resistance that have developed against currently used antifungal medications.

Accordingly, in an embodiment, the present subject matter relates to a composition comprising an aqueous leaf extract of *Desmidorchis retrospiciens* (DR) mixed with silver nanoparticles biosynthesized with an aqueous leaf extract of *Desmidorchis retrospiciens* (DR-AgNPs).

According to an embodiment, the present subject matter relates to a method of preparing a silver nanoparticle nanocomposite comprising adding an aqueous leaf extract of *Desmidorchis retrospiciens* to an aqueous silver nitrate solution to obtain a mixture; heating the mixture with constant stirring to form *Desmidorchis retrospiciens*-silver nanoparticles (DR-AgNPs); separating the silver nanoparticles from the mixture; and obtaining the silver nanoparticle nanocomposite.

According to an embodiment, the present subject matter relates to a method for treating histoplasmosis in a patient, comprising administering a composition as described herein to a patient in need thereof.

These and other features of the present subject matter will become readily apparent upon further review of the following specification.

BRIEF DESCRIPTION OF DRAWINGS

FIG. 1 shows the particle size distribution of the biosynthesized DR-AgNPs.

FIGS. 2A-2B are SEM (FIG. 2A) and 3D (FIG. 2B) images of the biosynthesized DR-AgNPs.

FIG. 3 is a graph of a time kill assay showing the effect of the plant extract (DR), DR-AgNPs, and DR-AgNPs/DR on the growth of *H. capsulatum*.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It will be understood by those skilled in the art with respect to any chemical group containing one or more substituents that such groups are not intended to introduce any substitution or substitution patterns that are sterically impractical and/or physically non-feasible.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

As described herein, "room temperature" means a temperature of about 25° C.

The present subject matter relates to a novel composition for the treatment of histoplasmosis. Specifically, the present subject matter relates to the inhibition of fungal growth by using a composition of green biosynthesized silver nanoparticles using leaf extract of Desmidorchis retrospiciens as a novel antifungal therapy, thus reducing side effects and resistance that have developed against currently used antifungal medications.

Accordingly, in an embodiment, the present subject matter relates to a composition comprising an aqueous leaf extract of Desmidorchis retrospiciens (DR) mixed with silver nanoparticles biosynthesized with an aqueous leaf extract of Desmidorchis retrospiciens (DR-AgNPs).

In an embodiment in this regard, the present compositions may comprise both about 100 μg/ml of the aqueous leaf extract of D. retrospiciens mixed with 100 μg/ml of the silver nanoparticles biosynthesized using an aqueous leaf extract of D. retrospiciens and capped with its phytochemicals. In an embodiment, the ratio of the two components is 1:1 (volume/volume).

Figure 1:
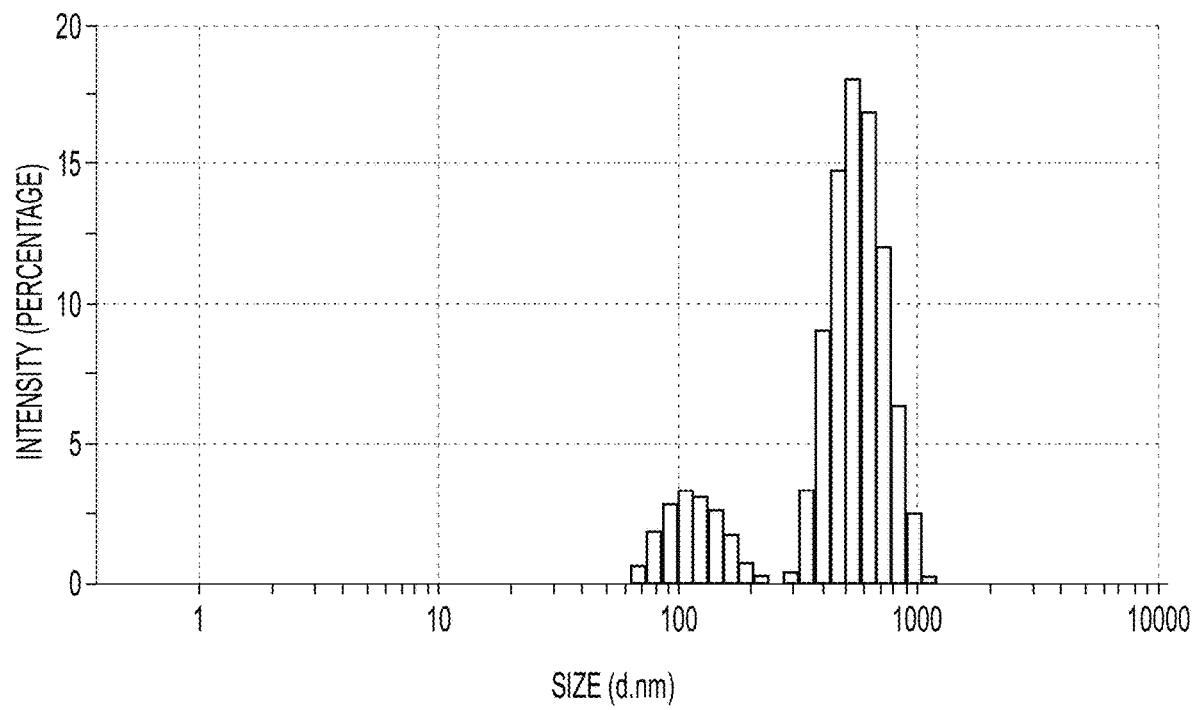

In certain embodiments, dynamic light scattering (DLS) can be used to determine the diameter, size, distribution, and the like of the nanoparticles in the aqueous solution. In this regard, in one embodiment, the DR-AgNPs nanoparticles can have an average particle diameter of about 500 to about 600 nm, about 525 to about 575 nm, or about 558 nm. Similarly, the DR-AgNPs nanoparticles can have a polydispersity index of about 0.580. See FIG. 1 in this regard.

Figure 2A:
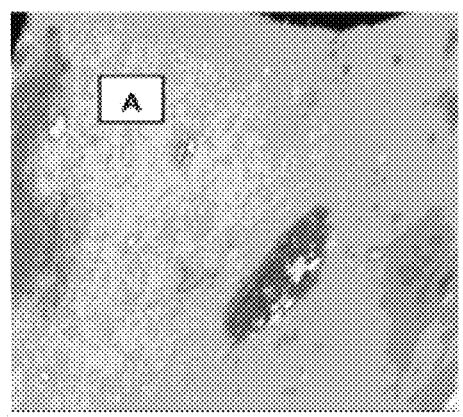
Figure 2B:
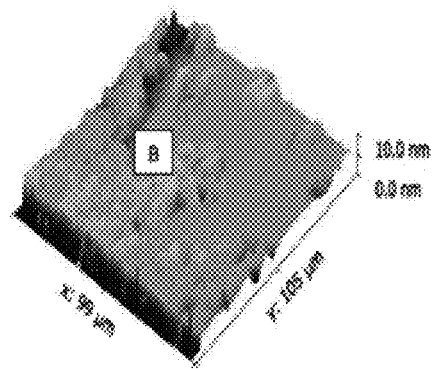

As shown in FIG. 2A, the present DR-AgNPs nanoparticles can be spherical in shape and can have an approximate size of about 10 nm.

In another embodiment, the DR-AgNPs nanoparticles can contain functional groups ranging from about 720 to about 3413 $cm^{-1}$. Non-limiting examples of the functional groups that can be included in the present nanoparticles include O—H (Alcohols, Phenols), C—H (Alkenes), C—H (Phenyl ring), $NO_2$ (Nitro compound), and N—H and C—N(Amines). While the broad peak at 3003 $cm^{-1}$ corresponded to the N—H group of the peptide linkage occurring in the leaf extract, there was a dominance of alcohol and amine groups.

In another embodiment, the present compositions can be prepared by mixing the aqueous leaf extract of D. retrospiciens (DR) with the present biosynthesized silver nanoparticles (DR-AgNPs). In certain embodiments, these two components can be combined in an 1:1 ratio (volume/volume).

According to an embodiment, the present subject matter relates to a method of preparing a silver nanoparticle nanocomposite comprising adding an aqueous leaf extract of Desmidorchis retrospiciens to an aqueous silver nitrate solution to obtain a mixture; heating the mixture with constant stirring to form Desmidorchis retrospiciens-silver nanoparticles (DR-AgNPs); separating the silver nanoparticles from the mixture; and obtaining the silver nanoparticle nanocomposite.

In one embodiment in this regard, 20 mL of aqueous leaf extract of D. retrospiciens can be added to 200 mL of an 1 mM aqueous silver nitrate solution, followed by heating at about 80° ° C. to about 90° C., or about 85° C., with constant stirring. In an embodiment, the heating can occur for at least about 4 hours, or about 4 hours.

During the heating/stirring step, the formation of the AgNPs can be detected by the change in color of the mixture from yellow to dark brown.

In an embodiment, the nanoparticles can be separated from the mixture using centrifugation at about 20,000×g for about 25 min.

In certain embodiments, the centrifugation process can be conducted once, twice, or three or more times to ensure removal of the free silver associated with the DR-AgNPs. The final green biosynthesized AgNPs can be denoted as DR-AgNPs. In certain embodiments, once formed, the DR-AgNPs can be freeze-dried and then stored at 4° C. until they are ready for further use.

According to an embodiment, the present subject matter relates to a method for treating histoplasmosis in a patient, comprising administering a composition as described herein to a patient in need thereof.

In this regard, upon administration to a patient, the present compositions can control growth of Histoplasma capsulatum in the patient. In additional embodiments, the combination of the present aqueous leaf extract of D. retrospiciens (DR) with the present biosynthesized silver nanoparticles (DR-AgNPs) can result in a synergistic effect in treating the patient. That is, the DR-AgNPs/DR can display synergistic antifungal potential against H. capsulatum.

In certain embodiments, the present compositions can be formulated for intravenous administration to the patient. In one embodiment, the present compositions are formulated for intravenous (IV) injection to the patient, with citrate (CT) and polyvinyl pyrrolidone (PVP) coated DR-AgNPs/DR. In certain embodiments, each injection can comprise a unit dosage of about 10 mg/kg of body weight of the active.

Further in this regard, another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients can, for example, include water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

The present teachings are illustrated by the following examples.

EXAMPLES

Example 1

Preparation of Aqueous Leaf Extract of *D. retrospiciens*

The leaves of *D. retrospiciens* were washed thoroughly with distilled water and allowed to dry in the shade at room temperature. The dried leaves were crushed using an electric lab blender to make a fine powder. 500 mL of distilled water was added to 50 g of leaf powder and the mixture was heated at 70° C. for 3 h with continuous stirring. The resultant extract was then filtered through Whatman filter paper no. 1. The extract was stored at 4° C. until further use.

Example 2

Green Biosynthesis of Silver Nanoparticles

For the green synthesis of AgNPs, 20 mL of the aqueous leaf extract of *D. retrospiciens* of Example 1 was added to 200 mL of 1 mM aqueous silver nitrate solution, followed by heating at 85° C. for 4 h with constant stirring. The formation of the AgNPs was detected by the change in color from yellow to dark brown. The nanoparticles were separated using centrifugation at 20,000×g for 25 min. This process was repeated twice to get rid of free silver associated with DR-AgNPs. The final green biosynthesized AgNPs were denoted as DR-AgNPs, which were freeze-dried and then stored at 4° C. until further use.

Example 3

Preparation of DR-AgNPs/DR Composition

Aqueous leaf extract of *D. retrospiciens* (100 µg/ml) of Example 1 was mixed with the green biosynthesized silver nanoparticles (50 µg/ml) of Example 2. The ratio of the two components is (1:1) (volume/volume).

Example 4

Antifungal Activity

The antifungal potential of the leaf extract (DR), DR-AgNPs, and DR-AgNPs/DR were investigated by measuring the radial growth inhibition. The DR-AgNPs displayed a higher antifungal action where the MIC of DR-AgNPs and plant extract were 50 and 100 µg/ml, respectively. Interestingly, DR-AgNPs/DR displayed synergistic antifungal potential against *H. capsulatum*.

Antifungal susceptibility testing of both yeast and mycelial forms was also determined by broth microdilution using CLSI documents. The 10 days of hyphal growth on Sabouraud's dextrose agar at 28° C. was used for preparing the inoculum for the mycelial form, which was adjusted to an optical density at 530 nm of 0.20 to 0.24, diluted 1:10 in RPMI 1640 medium to obtain 2.5×105 to 5×105 conidia/hyphal fragments per ml. The plates were incubated at 28° C. for 120 h. The yeast inocula, prepared from growth on BHI agar, were adjusted to 5 McFarland standard, diluted 1:100 in RPMI 1640 to obtain 1×105 to 2.5×105 CFU/ml, and the plates were incubated at 37° C. for 72 to 96 h. The antifungals tested were DR, DR-AgNPs, and DR-AgNPs/DR.

Figure 3:
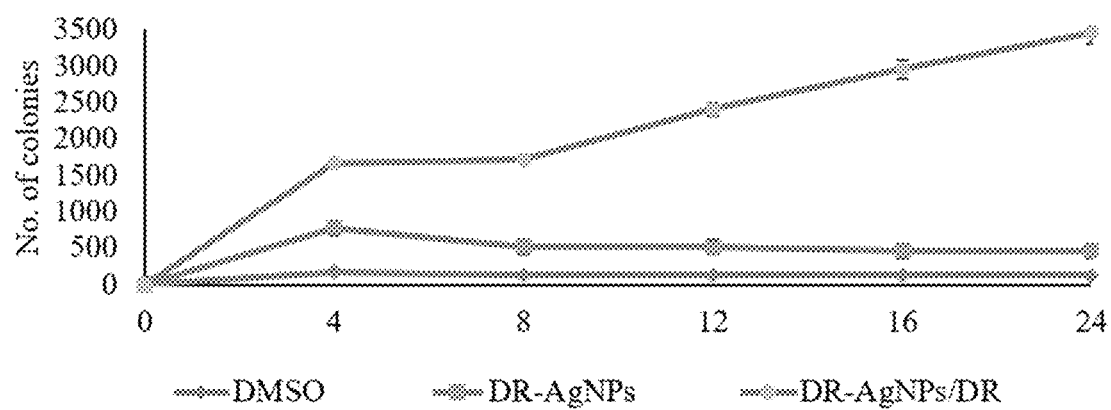

The time-kill curves showed the fungistatic action of both DR-AgNPs and leaf extract (DR) at 50 and 100 µg/mL, respectively, on the growth of *H. capsulatum* cells (FIG. 3). After 8 h of incubation, DR-AgNPs/DR completely repressed the growth of *H. capsulatum*. Therefore, DR-AgNPs/DR exhibited synergetic antifungal action than either the DR-AgNPs or the plant extract.

It is to be understood that the methods and compositions not limited to the specific embodiments described above but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for treating histoplasmosis in a patient, comprising administering a composition to a patient in need thereof, wherein the composition comprises an aqueous leaf extract of *Desmidorchis retrospiciens* (DR) mixed with silver nanoparticles biosynthesized with an aqueous leaf extract of *Desmidorchis retrospiciens* (DR-AgNPs).

2. The method of claim 1, wherein the composition is administered as an intravenous injection.

3. The method of claim 1, wherein the composition comprises the aqueous leaf extract of *Desmidorchis retrospiciens* (DR) and the silver nanoparticles biosynthesized with an aqueous leaf extract of *Desmidorchis retrospiciens* (DR-AgNPs) in a ratio of about 1:1, volume/volume.

4. The method of claim 1, comprising administering about 10 mg/kg body weight of the *Desmidorchis retrospiciens* (DR) and the silver nanoparticles biosynthesized with an aqueous leaf extract of *Desmidorchis retrospiciens* (DR-AgNPs).

5. The method of claim 1, wherein the *Desmidorchis retrospiciens* (DR) and the silver nanoparticles biosynthesized with an aqueous leaf extract of *Desmidorchis retrospiciens* (DR-AgNPs) act synergistically to treat the histoplasmosis.

6. The method of claim 1, wherein the administration of the composition provides synergistic antifungal activity against *H. capsulatum*.

* * * * *